United States Patent [19]

Agnone

[11] Patent Number: 4,828,492
[45] Date of Patent: May 9, 1989

[54] DENTAL IMPLANT

[76] Inventor: Frank A. Agnone, 1539 Wyoming Ave., Scranton, Pa. 18509

[21] Appl. No.: 860,206

[22] Filed: May 6, 1986

[51] Int. Cl.$^4$ ............................................. A61C 8/00
[52] U.S. Cl. .................................. 433/173; 433/201.1
[58] Field of Search ............ 433/173, 174, 175, 201.1, 433/176; 623/16, 17

[56] References Cited

U.S. PATENT DOCUMENTS

| | | | |
|---|---|---|---|
| 3,082,525 | 3/1963 | Christensen | 433/174 |
| 3,436,826 | 4/1969 | Edelman | 433/173 |
| 4,379,694 | 4/1983 | Riess | 433/173 |
| 4,488,875 | 12/1984 | Niznick | 433/173 |

Primary Examiner—Robert Peshock
Assistant Examiner—Adriene J. Lepiane
Attorney, Agent, or Firm—Webb, Burden, Robinson & Webb

[57] ABSTRACT

The present dental implant comprises a hollow perforate trans-mandibular or -maxillary bolt, adapted for receiving a trephined core of bone, for transverse implantation in the maxilla or mandible in conjunction with contiguous straps. These contiguous straps tighten against the periosteum, encase the alveolar ridge and thread through an adjustable implant receptor having a receptor site for abutment thereon. As a result of the combined hollow bolt/strap structure, the dental implant achieves stability by means of (1) medullary bony union with the perforate bolt; (2) subperiosteal bony union with the perforate contiguous straps; and (3) mechanical union afforded by the alveolar-ridge-encasing structure defined by the bolt and contiguous straps. The dental implant thus positioned can be used to support teeth, partial dentures or an entire dental arch. Implant materials may be those known in the art but are preferably biologically inert stainless steel and/or titanium alloys.

19 Claims, 2 Drawing Sheets

DENTAL IMPLANT

FIELD OF THE INVENTION

The present invention relates to mandibular or maxillary implants for the temporary or permanent retention or artifical dentures and related prostheses.

INTRODUCTION

Mandibular and maxillary bone implants, to which denture and other structures are anchored, are increasingly widely used in restorative oral and maxillofacial surgery. Unfortunately, many implant arrangements have failed, within a period of a few years from implantation, as a result of the physical, metabolic and other physiologic forces which are exerted upon such implants. Generally speaking, only those implants which enable a high degree of bony union, i.e., growth of surrounding bone into and around the implant itself, are satisfactory for general use.

BACKGROUND OF THE INVENTION

A number of dental implants are disclosed in various United States patents, U.S. Pat. No. 3,436,826 to Edelman discloses a dental implant in which a pin is adapted to be inserted transversely through the mandible in such a way as to receive a perpendicular threaded fastener. A drill jig may be temporarily positioned over the mandible, but the jig forms no part of the permanent implantation. U.S. Pat. No. 4,121,340 to Patrick discloses a dental implant having a bladevent body and a relatively wide straddling subperiosteal frame; and abutment post appends the subperiosteal frame and thus is only indirectly attached to the bladevent body, to prevent unwanted invagination of the oral epithelium. U.S. Pat. No. 4,084,318 to McEachern discloses a method wherein a cavity is cut into the mandible or maxilla from either side. A second bore is then drilled vertically into the bone structure to intersect the first-formed cavity. A rectangular anchor base is laterally inserted into the first cavity and a shank and an anchor post are mounted thereupon. The non-circular cross section of the rectangular anchor base resists torsional strain applied to a shank mounted therein.

U.S. Pat. No. 4,531,916 to Scantlebury et al. discloses a dental implant having a root structure, a cervical segment, and a porous gingival interface; this interface, which is made of expanded polytetrafluoroethylene, facilitates tissue ingrowth and discourages bacterial penetration. U.S. Pat. No. 4,244,689 to Ashman discloses polymeric plastic implants, for endosteal and periosteal applications, in which nontoxic leachable substances such as sodium chloride crystals having a controlled particle size are incorporated in the prepolymer-liquid monomer mixture prior to implantation. After heat polymerization without an initiator, the leachable substance is removed from the plastic implant to provide porosity for tissue ingrowth.

Prior art devices fail to provide maximum stability, unfortunately, because the implant typically integrates only one structure with the maxilla or mandible and thus promotes only limited bony union. A need remains, therefore, for a dental implant which not only provides an implant receptor, in the general manner of prior art devices, but which also provides maximum stability and permanence as a result of both mechanical and bony union at a plurality of maxillary/mandibular sites.

BRIEF DESCRIPTION OF THE INVENTION

In order to meet this need, the present dental implant comprises a hollow perforate trans-mandibular or -maxillary bolt, adapted for receiving a trephined core of bone, for transverse implantation in the maxilla or mandible in conjunction with contiguous straps. These contiguous straps tighten against the periosteum, encase the alveolar ridge, and thread through an adjustable implant receptor having a receptor site for abutment thereon. As a result of the combined hollow bolt/strap structure, the dental implant achieves stability by means of (1) medullary bony union with the perforate bolt; (2) subperiosteal bony union with the perforate contiguous straps; and (3) mechanical union afforded by the alveolar-ridge-encasing frame structure defined by the bolt and contiguous straps. The dental implant thus positioned can be used to support single teeth, partial dentures or an entire dental arch. Implant materials may be any of those known in the art, but are preferably biologically inert stainless steel and/or titanium alloys.

DETAILED DESCRIPTION OF THE INVENTION

The implanted structure of the present dental implant is best understood by means of the method in which the surgical implantation takes place, First, the muco-periosteum is reflected from the crest of the mandibular or maxillary alveolar ridge from both the buccal and the lingual direction. Vertical relief incisions are made at both ends of the incisions toward the apex of the roots. A drill site is selected either at a midpoint between the crest of the mandibular ridge and the inferior border of the mandible or at a midpoint between the crest of the maxillary ridge and the sinus or nasal floor of the maxilla. A hollow shank water-cooled trephine drill is used to excise a core of bone from the buccal cortical plate to the lingual cortical plate and through the medullary bone. The diameter of the core of bone should be between 3.0 and 5.0 mm. with a preferred diameter of 5.0 mm. for use with a mandible of average size. (The larger diameters are generally preferred with edentulous, i.e., toothless, jaws.)

The excised core of bone is removed from the trephine drill in one piece and is placed in sterile saline. A gauge is used to measure the buccal-lingual width in millimeters and a hollow bolt of corresponding diameter and length is selected. The hollow bolt has an additional distinguishing feature besides its longitudinally hollow structure; the hollow walls of the shaft of the bolts are perforate, i.e., have a perforated structure whereby the walls contain a plurality of apertures therein. (These perforations may be perforations, specifically, or may be discontinuities, generally. Applicant for convenience therefore defines "perforate" as "having a plurality of apertures therein," regardless of the origin of the apertures.) The excised bone core is packed into the hollow perforate bolt.

The hollow perforate bolt is then inserted into the drill hole by threading it through the subperiosteal straps on either side of the drill hole. The two subperiosteal straps are perforate straps or bands which are designed to be flattened against the bone, brought to the crest of the alveolar ridge, threaded through an implant receptor and tightened with a fastening means. The mucoperiosteum is then sutured by means known in the art, and the dental abutment, adapted to hold either temporary or permanent restorations, is selected and cemented to its receptor site.

Figure 1:
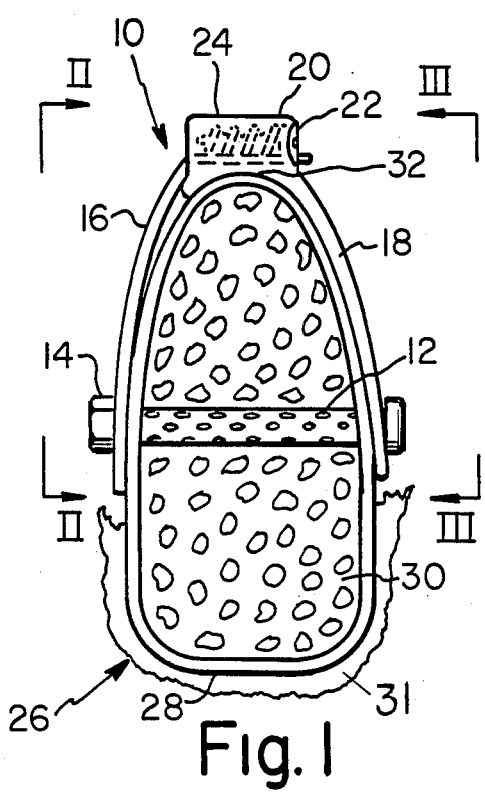
FIG. 1 is a sectional view of the dental implant 10 as mounted on the mandible 26.

An illustrative embodiment of the present dental implant, which results from the above surgical procedure, is illustrated in the accompanying figures. Referring now to FIG. 1, the dental implant 10 is affixed to the mandible 26 by means of a hollow perforate bolt 12 which contains the excised trephined core of bone. The hollow perforate bolt 12 extends transversely through the mandible 26, including the periosteum 28 and the medullary bone 30, and is secured by the nut 14. The lowermost portion of the periosteum 28 is shown adjacent a broken-away area of surrounding soft tissue 31. First and second contiguous straps 16 and 18 having bolt-receiving apertures therein are threaded onto the bolt and are positioned flat against and tautly adjacent the periosteum 28. The first and second contiguous straps 16 and 18 are secured, at the crest of the alveolar ridge 32, to the implant receptor 20. As illustrated, contiguous strap 18 is integrally formed with the implant receptor 20 and contiguous strap 16 is threaded through an aperture in the implant receptor 20 and tightened by means of implant receptor tightening means 22, shown as a transverse screw which cooperates with ridges on the adjacent surface of contiguous strap 16. Selective tightening of the hollow perforate bolt 12 and the nut 14, along with tightening of the implant receptor tightening means 22, yields an alveolar-ridge-encasing structure which performs as a mechanical clamp and which contacts, for integration therewith, both the medullary bone and the periosteal surface of the host site.

The structure illustrated in FIG. 1 demonstrates increased stability, over dental implants known in the art, as a result of (1) endosseous bone union of the medullary bone with the excised/repacked core via the hollow perforate bolt 12; (2) subperiosteal bone union of the first and second contiguous straps 16 and 18 with the periosteum 28; and (3) mechanical fixation of an overall frame- or clamp-like implant through and around the ridge-containing half of the mandible or maxilla.

The dental implant 10 of FIG. 1 is adapted to support a dental abutment via the receptor site for abutment 24. The receptor site for abutment 24 as shown is an aperture in the implant receptor into which the base of a dental abutment may be cemented or otherwise mounted. Temporary crowns or bridges may be cemented to the dental abutment, and permanent restorations may be completed after an appropriate healing period (i.e., two weeks).

Figure 2:
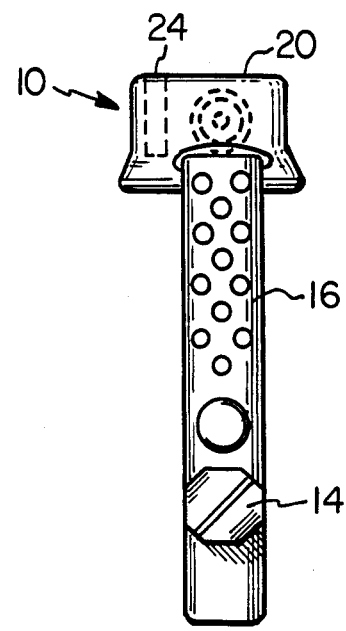
FIG. 2 is a side elevational view of the dental implant taken along line II—II of FIG. 1.
Figure 3:
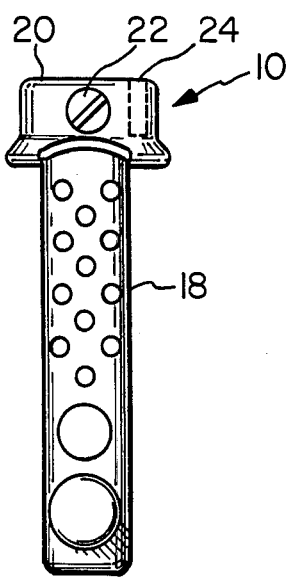
FIG. 3 is a side elevational view of the dental implant taken along line III—III of FIG. 1.

Referring now to FIG. 2, a side elevational view of the dental implant 10 is shown along lines II—II of FIG. 1. FIG. 2 illustrates the perforations (i.e., plurality of apertures) in the contiguous strap 16 and shows more particularly the receptor site for abutment 24. FIGS. 2 and 3 together illustrate that the contiguous straps 16 and 18 may each have more than one bolt-receiving aperture therein; such configuration both encourages subperiosteal ingrowth and minimizes the required inventory of contiguous straps of various lengths.

Figure 4:
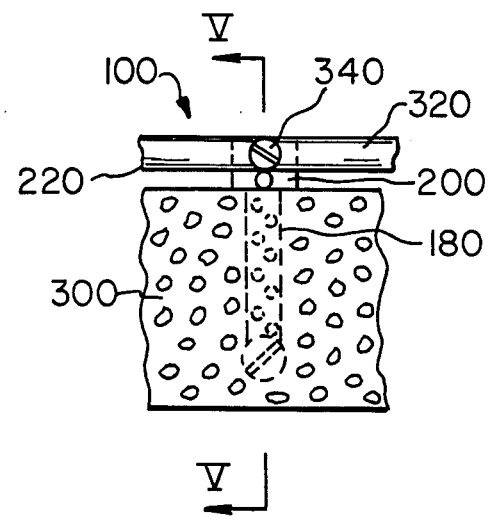
FIG. 4 is a sectional view of the alternate embodiment of the invention, illustrating the denture support-retention blade 320.
Figure 5:
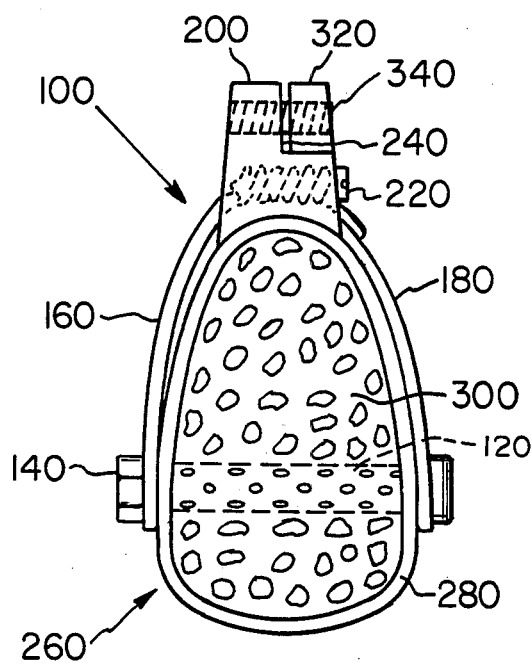
FIG. 5 is a sectional view of the alternate embodiment of the invention taken along line V—V of FIG. 4.
Figure 6:
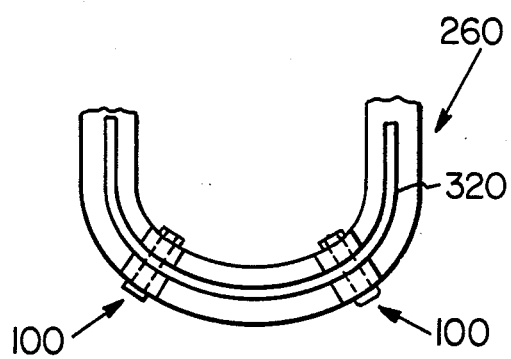
FIG. 6 is a plan view of an exposed mandible showing dental implants 100 having the denture support-retention blade 320 mounted thereon.

In a second embodiment of the invention, a particularly configured receptor site for abutment is especially adapted to receive the particular dental abutment known as the denture support-retention blade 320. This embodiment of the invention is illustrated in FIGS. 4–6. (In further embodiments of the invention, the receptor site for abutment may have a number of shapes and configurations, including apertures of various shapes having alternately smooth or threaded interior surfaces.)

Referring now to FIG. 5, the dental implant 100 is shown as mounted within and onto mandible 260 by means of a hollow perforate bolt 120 having a trephined core of bone therein secured between first and second contiguous straps 160 and 180 and nut 140 to secure an implant receptor 200 to the mandible. The implant receptor 200 has an implant receptor tightening means 220 thereon which, as in the first embodiment of the invention, includes a screw which tightens the straps by means of cooperating grooves on the adjacent strap surfaces. In this embodiment of the invention, however, the implant receptor 240 has a modified structure adapted to receive a denture support-retention blade 320. (A side elevational view of the denture support-retention blade is shown in FIG. 4.) The recessed receptor site for abutment 240 therefore receives the denture support-retention blade 320 by means of the denture support-retention blade fastening means 340 as shown in FIG. 5. As illustrated in FIG. 5, one or more dental implants 100 function to anchor an extended curved denture support-retention blade 320 for full arch replacements in the edentulous jaw.

Figure 7:
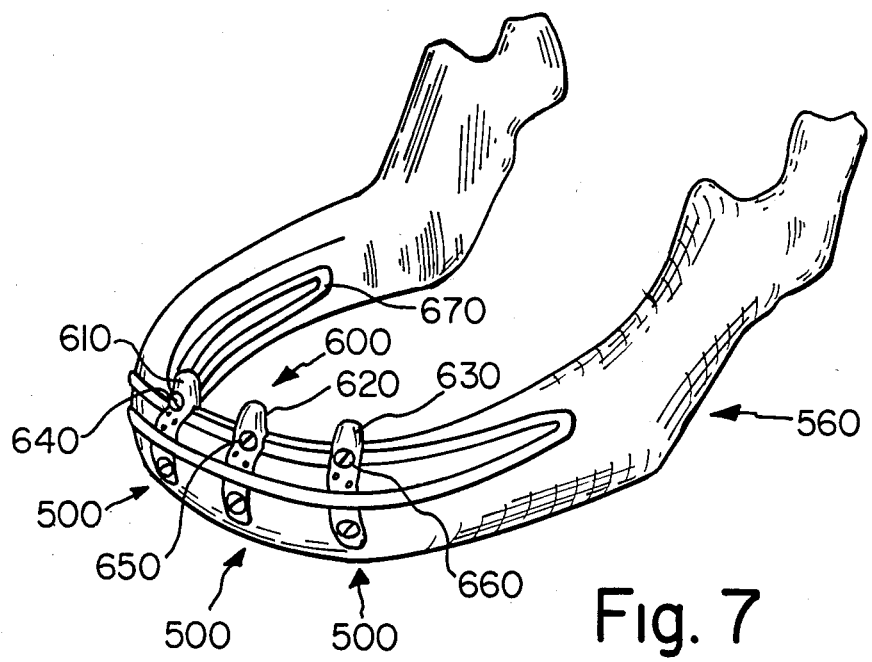
FIG. 7 is a perspective view of an exposed mandible having yet another embodiment of the invention, a custom-fit dental abutment superstructure, mounted thereon.

Referring now to FIG. 7, yet another embodiment of the invention is illustrated. The dental implants 500 are shown in association with the exposed mandible 560. Mounted atop the dental implants 500 is the dental abutment superstructure 600. The dental abutment superstructure 600 is fabricated as a unit prior to surgery, usually from a wax impression taken prior to surgery. The dental abutment superstructure 600 includes, as shown, three abutment posts 610, 620, and 630, three receptor tightening means 640, 650 and 660, and a custom-fit arrangement of a plurality of bands 670 which may fit snug against the mandible, extend into the oral cavity as an exposed abutment track, or both. The arrangement of bands, abutments, and interconnections may be prepared, following the wax impression, to accommodate the specific needs of the individual patient. As shown in the embodiment illustrated in FIG. 7, the abutment posts 610, 620 and 630 will extend into the oral cavity after surgery is complete.

The implantation of the subject dental implant is a surgical procedure well with the surgical skills of the ordinary general practitioner. The procedure may be performed under local anesthesia and thus may be performed in the dental office without need for hospitalization of the patient. With practice, a practitioner can complete a single implant in fifteen minutes and a complete dental arch in one office visit. If necessary, for example due to fracture of the jaw, the dental implant may be removed without disfigurement to the patient.

Materials suitable for use in the present dental implant are the alloys and polymers generally accepted for use in the dental implant art. However, because the present dental implant has particular stability and concommitant longevity in position, the avoidance of cytotoxic or otherwise biologically active structural materials is essential. For this reason, the biologically inert stainless steel and titanium alloys known in the implant art are the preferred materials for use in the present invention.

Various changes may be made to the embodiments of the invention described above without affecting the identity or scope of the present invention. For example, although for convenience the invention has been described in terms of a transverse bolt and contiguous, alveolar-ridge-encasing straps, the disclosed and claimed invention encompasses any trans-mandibular or -maxillary (i.e., trans osseous) hollow perforate shaft-like extension in combination with an alveolar-ridge-encasing perforate subperiosteal structure. As a result, the entire implant need not be constructed of a bolt and straps per se. Likewise, one contiguous strap need not be integrally molded with the implant receptor 20, but may instead thread and fasten therein by means known in the art, i.e., via a second implant receptor tightening means or the like. Finally, although the hollow perforate bolt will generally have a diameter between 3.0 and 5.0 mm., dimensions for the associated structures will and should vary to accommodate the specific mandibular or maxillary anatomy of the patient.

Although the invention has been described with reference to particular materials and particular processes, the invention is to be limited only insofar as is set forth in the accompanying claims.

I claim:

1. A mandibular or maxillary dental implant, comprising:
   a trans osseous shaft;
   a means for encasing the alveolar ridge being interconnected with said shaft; and
   an implant receptor, whereby said shaft and said means for encasing the alveolar ridge are implanted together to secure the implant receptor in place.

2. The dental implant of claim 1 wherein said shaft is hollow.

3. The dental implant of claim 2 wherein said shaft is perforate.

4. The dental implant of claim 1 wherein said means for encasing the alveolar ridge includes at least one strap.

5. The dental implant of claim 4 wherein said strap is perforate.

6. The dental implant of claim 5 wherein said strap is adjustable in length.

7. The dental implant of claim 1 wherein said implant receptor is adapted to interlock with said means for encasing the alveolar ridge.

8. The dental implant of claim 1 wherein said implant receptor is adapted to adjustably interlock with said means for encasing the alveolar ridge.

9. The dental implant of claim 1 wherein said implant receptor has a receptor site for abutment thereon.

10. The dental implant of claim 9 wherein said receptor site for abutment is an aperture within said implant receptor.

11. The dental implant of claim 10 wherein said aperture within said implant receptor supports a dental abutment.

12. The dental implant of claim 9 wherein said receptor site for abutment is a recessed area within said implant receptor.

13. The dental implant of claim 11 wherein siad recessed area within said implant receptor supports a denture support-retention blade by means of a denture support-retention blade fastening means.

14. The dental implant of claim 1 wherein said trans osseous shaft is a hollow perforate trans osseous bolt having a nut in combination therewith and further having attached thereto said means for encasing the alveolar ridge adjacent said shaft, wherein said means for encasing the alveolar ridge further comprises a pair of contiguous perforate straps adapted to secure to an implant receptor positioned at the crest of said alveolar ridge.

15. The dental implant of claim 14 wherein said implant receptor supports a dental abutment.

16. The dental implant of claim 15 wherein said bolt and said straps encase the alveolar ridge of the human mandible when in use.

17. The dental implant of claim 15 wherein said bolt and said straps encase the alveolar ridge of the human maxilla when in use.

18. The dental implant of claim 14 wherein said implant receptor has a recessed receptor site for abutment thereon which supports a denture support-retention blade by means of a denture support-retention blade fastening means.

19. The dental implant of claim 14 wherein said implant receptor supports a dental abutment superstructure.

* * * * *